US006448425B1

(12) United States Patent
Gedon et al.

(10) Patent No.: US 6,448,425 B1
(45) Date of Patent: Sep. 10, 2002

(54) PREPARATION OF N-SUBSTITUTED AMINOORGANOSILANES

(75) Inventors: Steven C. Gedon, Williamstown, WV (US); Melinda Hale, Belmont, WV (US)

(73) Assignee: Crompton Corporation, Middlebury, CT (US)

( * ) Notice: Subject to any disclaimer, the term of this patent is extended or adjusted under 35 U.S.C. 154(b) by 0 days.

(21) Appl. No.: 10/076,378

(22) Filed: Feb. 19, 2002

(51) Int. Cl.$^7$ .................................................. C09F 7/10
(52) U.S. Cl. ...................................................... 556/413
(58) Field of Search ......................................... 556/413

(56) References Cited

U.S. PATENT DOCUMENTS

| | | | |
|---|---|---|---|
| 4,481,364 A | 11/1984 | Chu et al. | 556/413 |
| 4,526,996 A | 7/1985 | Kilgour et al. | 556/413 |
| 4,801,673 A | 1/1989 | Bosch et al. | 528/34 |
| 4,892,918 A | 1/1990 | Ryang | 528/15 |
| 5,874,622 A | 2/1999 | Breitscheidel et al. | 564/450 |
| 6,248,924 B1 | 6/2001 | Ruhl et al. | 564/450 |
| 6,268,501 B1 | 7/2001 | Kiel | 546/185 |

FOREIGN PATENT DOCUMENTS

| | | |
|---|---|---|
| CZ | 165746 | 11/1976 |
| CZ | 245443 | 10/1986 |
| EP | 88-115109 | 9/1988 |
| EP | 302672 A1 | 2/1989 |
| EP | 321174 A2 | 6/1989 |
| JP | 04210693 | 7/1992 |

OTHER PUBLICATIONS

Shi B. et al., Nanjing Shida Zuebao, Ziran Kexueban, 22(1): Abstract (1999).
Chernyshev, E.A. et al., Zh. Obshch. Khim., 54(9): Abstract (1984).

Primary Examiner—Paul F. Shaver
(74) Attorney, Agent, or Firm—Michael P. Dilworth

(57) ABSTRACT

A process is disclosed for the synthesis of N-cycloalkylaminoalkylsilanes, wherein the process comprises hydrogenating the corresponding N-arylaminoalkylsilanes in the presence of a catalytically effective amount of a supported or unsupported catalyst selected from the group consisting of palladium, platinum, nickel, rhenium, rhodium, ruthenium, copper chromite, and mixtures of the foregoing.

10 Claims, No Drawings

PREPARATION OF N-SUBSTITUTED AMINOORGANOSILANES

BACKGROUND OF THE INVENTION

1. Field of the Invention

The present invention is related to a process for the preparation of secondary and/or tertiary aminoorganosilanes by the catalytic hydrogenation of N-aryl substituted aminoorganosilanes and/or iminoorganosilanes in the presence of a suitable precious metal catalyst, such as rhodium, ruthenium, and the like, and hydrogen.

2. Description of Related Art

Aminopropyltrialkoxysilanes and aminoalkylalkoxysilanes find general utility as potential glass-plastic coupling agents, bonding aids, additives to phenolic binder/foundry mixtures, adhesion promoters for vinyl plastisols, polyurethane elastomers, and epoxy and acrylic-based inks. The application of secondary and/or tertiary aminoorganosilanes in these markets is also well known to those skilled in the art; they are an important class of compounds and the subject of considerable commercial interest.

N-cyclohexyl-3-aminopropyltrimethoxysilane and the like are generally prepared by the direct reaction of cyclohexylamine derivatives with 3-chloropropyltrimethoxysilane. See, for example, Czech. Patent No. 245,443; U.S. Pat. No. 4,801,673 and Shi, B. et al., *Nanjing Shida Xuebao, Ziran Kexueban*, 22(1):64–67 (1999). This approach typically requires a large excess of the cyclohexylamine, e.g., five molar equivalents, and generates an equivalent of hydrochloride salt, which must be either recycled or disposed of as a hazardous waste. Moreover, the variety of useful cyclohexylamine derivatives that can be used in the above process is limited in number and those that are available are often rather expensive.

Alternatively, preparation of N-cyclohexyl-3-aminopropyltrimethoxysilane from the hydrosilation of allyl amines with SiH-funtional organo silicones and silanes has also been reported. See, for example, U.S. Pat. No. 4,481,364; U.S. Pat. No. 4,892,918; EP 88-115109; EP 302672 A2; EP 321174 A2; JP 04210693; Czech. Patent No. CS 165746; and Chernyshev, E. A. et al., *Zh. Obshch. Khim.*, 54(9): 2031–2034 (1984).

U.S. Pat. No. 4,526,996 discloses a selective process for the production of N-substituted aminoalkylsilanes which comprises reacting a cyanoalkylsilane with a primary or secondary amine in the presence of a heterogeneous hydrogenation catalyst selected from the group consisting of rhodium, platinum and palladium.

U.S. Pat. No. 5,874,622 discloses a process for hydrogenating an aromatic compound in which at least one hydroxyl group is bonded to an aromatic ring or an aromatic compound in which at least one amino group is bonded to an aromatic ring, in the presence of a catalyst comprising as catalytically active component at least one metal of transition group I, VII or VIII of the Periodic Table applied to a support, wherein the catalyst is obtainable by a) dissolving the catalytically active component or a precursor compound thereof in a solvent, b) admixing the solution thus obtained with an organic polymer which is able to bind at least ten times its own weight of water, giving a swollen polymer, c) subsequently mixing the swollen polymer with a catalyst support material and d) shaping, drying and calcining the composition obtained in this way.

U.S. Pat. No. 6,248,924 discloses a process for the reaction of an organic compound in the presence of a catalyst comprising, as active metal, ruthenium alone or together with at least one Group Ib, VIIb, or VIIIb metal in an amount of from 0.01 to 30 wt %, based on the total weight of the catalyst, applied to a support, wherein from 10 to 50% of the pore volume of the support comprises macropores having a pore diameter in the range of from 50 nm to 10,000 nm and from 50 to 90% of the pore volume of the support comprises mesopores having a pore diameter in the range of from 2 to 50 nm, the sum of said pore volumes being 100%, and said catalyst as such.

U.S. Pat. No. 6,268,501 discloses hydroxyethylcyclohexanes which can optionally contain a nitrogen atom in the cyclohexane ring that are obtained selectively by catalytic hydrogenation of the corresponding hydroxyethylbenzene or hydroxyethylpyridines when ruthenium, which has been treated before use with a reducing agent, is used as catalyst.

SUMMARY OF THE INVENTION

The present invention relates to a method for producing a new class of secondary and/or tertiary aminoorganosilanes from the reduction of the aromatic derivatives.

The present invention uses commercially available starting materials, such as N-phenyl-3-aminopropyltrimethoxysilane and the like, which undergo hydrogenation with a suitable commercially available catalyst, such as 5% rhodium on carbon, to produce N-cyclohexyl-3-aminopropyltrimethoxysilane derivatives in high yield.

In one aspect, the present invention is directed to a process for the hydrogenation of N-aryl aminoorganosilanes to the corresponding saturated products in the presence of a suitable catalyst, such as rhodium, ruthenium, and the like, under hydrogen pressure. The following equation is one example of such a hydrogenation reaction.

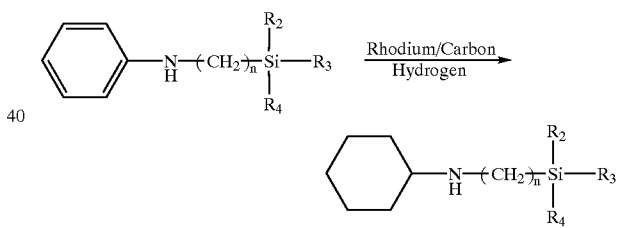

wherein $R_2$, $R_3$, and $R_4$ are independently selected from the group consisting of alkyl and alkoxy, provided that at least one of $R_2$, $R_3$, and $R_4$ is alkoxy, and n is 3.

For convenience, in the above equation a benzene ring has been used as the aryl group that is hydrogenated, but any other aryl group can as well be used in the practice of the present invention. Additionally, such aryl groups can, if desired, be substituted with any non-interfering moieties, e.g., alkyl, halo, and the like.

More specifically, the present invention is directed to a process for the synthesis of N-cycloalkylaminoalkylsilanes comprising hydrogenating the corresponding N-arylaminoalkylsilanes in the presence of a catalytically effective amount of a supported or unsupported catalyst selected from the group consisting of palladium, platinum, nickel, rhenium, rhodium, ruthenium, copper chromite, and mixtures of the foregoing.

DESCRIPTION OF THE PREFERRED EMBODIMENTS

Owing to the limited supply and high cost of both cyclohexylamine and/or N-allylcyclohexylamine, current methods for the preparation of N-cyclohexyl-3-aminopropyltrialkoxy silanes and the like are often quite expensive. Furthermore, the preparation of substituted aminoorganosilanes from the corresponding chlorosilanes, as heretofore known in the art, requires a large excess of the desired amine and results in the formation of an equivalent of a hydrochloride salt that must be either reclaimed or disposed of as a hazardous waste. The corresponding N-phenyl-3-aminopropytrialkoxysilanes, however, are commercially available and therefore a reliable raw material source.

A variety of methods have been reported in the prior art for the commercial preparation of N-aryl aminosilanes. Reduction of the aryl substituent of these N-aryl aminosilanes in the presence of a suitable catalyst has now been found to result in the corresponding cyclohexyl derivatives cleanly and in high yield. Moreover, the process of the present invention requires no solvents, occurs with high selectivity, and employs a catalyst that possesses sufficient activity for recycle. As a result, the preparation of N-cyclohexylaminoorganosilanes from these commercially available starting materials is a process that is more economically attractive and technically viable. In addition, the variety of known N-aryl derivatives that are amenable to this process as starting materials makes this process particularly attractive. Such derivatives include, but are not limited to, N-phenyl-γ-aminopropyltrimethoxysilane; N-phenyl-γ-aminopropyltributoxysilane; N-phenyl-γ-aminopropyltridodecyloxysilane; N-phenyl-γ-amino-2-methylpropyltrimethoxysilane; N-(4-trimethylsilyloxy)-phenyl-γ-aminopropyltrimethoxysilane; N-(4-N,N-dimethylaminophenyl)-γ-aminopropyltrimethoxysilane; 4,4'-oxybis{N-[3-(triethoxysilyl)propyl]-benzenamine); m-{ 3-(trimethoxysilylpropyl)amino }aniline; p-(3-(trimethoxysilylpropyl)amino }aniline; p-{3-(triethoxysilylpropyl)amino }aniline; 3,5-dimethyl-N-{3-(trimethoxysilyl)propyl }-benzenamine; 4-methyl-N-{3-(triethoxysilyl)propyl}benzenamine; 4-methyl-N-{3-(trimethoxysilyl)propyl}benzenamine, 4-methyl-N-{3-(trimethoxysilyl)propyl}-1,3-benzenediamine, N-{3-(triethoxysilyl)propyl}-1-naphthylamine, and the like.

The hydrogenation step in the process of the present invention is conducted at pressures in excess of atmospheric, for example, up to about 5000 psig, but generally pressures up to about 1000 psig are sufficient, with pressures in the range of from about 100 to about 600 psig being preferred. Hydrogenation temperatures may range from room temperature up to about 300° C. Depending upon the catalyst used and the pressure employed, temperatures greater than 100° and less than about 250° C. will generally suffice and temperatures less than 200° C., preferably about 150° to about 175° C., will often be adequate.

A wide range of catalysts known in the art can effect the desired hydrogenation. Examples of suitable catalysts include palladium, platinum, nickel, rhenium, rhodium, ruthenium, and copper chromite. Rhodium and ruthenium are preferred. Such catalysts may be used either supported or unsupported. If supported, they may be used on such supports as charcoal, carbonates, e.g., barium carbonate, kieselguhr, alumina, silica, and the like. Charcoal (i.e., carbon), carbonates, and alumina are preferred. Typically, the catalyst will comprise from about 2 to about 10% by weight of the total weight of catalyst and support, preferably about 5% by weight.

The catalyst can be employed in any catalytically effective amount. Generally, catalyst loadings of from about 0.1 up to 12 grams or greater per 1000 grams of silane are employed in the practice of this invention, but the preferred amounts are in the range of from 0.5 to 5 grams of catalyst per 1000 grams of silane, more preferably, about one gram of catalyst per 1000 grams of silane. Advantageously, the catalyst can be recycled.

Any aryl group can be employed as the aryl moiety of the N-arylaminoalkylsilane starting material and the choice of a particular aryl group will normally be dependent upon the identity of the desired cycloalkyl group of the product. Among the aryl groups that can be employed in the practice of the present invention are those derived from benzene, toluene, xylene, indene, naphthalene, methylnaphthalene, diphenyl, acenaphthene, fluorene, phenanthrene,anthracene, fluoranthene, pyrene, chrysene, thiophene, pyridine, picoline, quinoline, isoquinoline, quinaldine, indole, furan, acridine, carbazole, diphenylene oxide, hemimellitene, mesitylene, prehnitene, isodurene, durene, pentamethylbenzene, ethylbenzene, propylbenzene, cumene, butylbenzene, cymene, triethylbenzene, styrene, allylbenzene, stilbene, diphenylmethane, triphenylmethane, tetraphenylmethane, terphenyl, quaterphenyl, and the like. Any of these aryl moieties can have substituents bonded thereto that will not negatively affect the desired properties of the final cycloalkyl moiety-containing product. It is preferred that the aryl group be a derivative of benzene, i.e., a phenyl group.

Also included within the scope of the present invention is the hydrogenation of imino silanes to the corresponding cycloalkylaminoorganosilanes in the presence of a suitable catalyst as described above, e.g., rhodium. An example of such a reaction is the following:

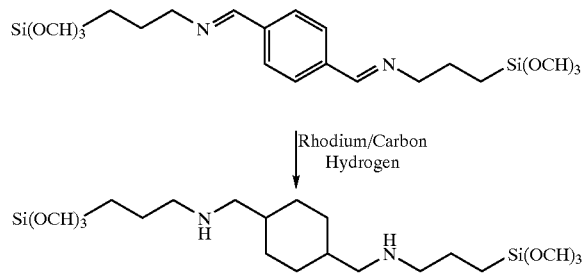

The hydrogenation process can be carried out continuously or batchwise. When the process is carried out continuously a portion of the hydrogenation product leaving the reactor can, if desired, be added the reactor feed upstream of the reactor. The remaining amount of hydrogenation product is retrieved.

The hydrogenating gases used can be arbitrary gases containing free hydrogen and exhibiting no harmful amounts of catalyst poisons, such as carbon monoxide. For example, reformer exhaust gases can be used. Pure hydrogen is preferably used as the hydrogenating gas.

Various features and aspects of the present invention are illustrated further in the examples that follow. While these examples are presented to show one skilled in the art how to operate within the scope of the invention, they are not intended in any way to serve as a limitation upon the scope of the invention.

EXAMPLES

Example 1

In a 2 liter autoclave equipped with magnadrive stirring, 1000 grams of N-phenyl-3-aminopropyltrimethoxysilane (Silquest Y-9669, OSi Specialties, Sistersville, W.Va.) was combined with 10 grams of 5% rhodium on carbon (Escat 340, Engelhard Corporation, Seneca, S.C.). The reactor was pressurized three times with hydrogen to 200 psig and vented before pressurizing to 300 psig and warming to 150° C. with 1000 rpm agitation. After sixty minutes the contents of the reactor were sampled and analyzed by GC. The product contained 91% N-cyclohexyl-3-aminopropyltrimethoxysilane and 5% N-phenyl-3-aminopropyltrimethoxysilane.

Example 2

In a 2 liter autoclave containing a stirrer, cooling coil, and sampling tube was added 974.5 grams of N-phenyl-3-aminopropyltrimethoxysilane and 12 grams of 5% rhodium on carbon. After purging the autoclave with nitrogen and then hydrogen, the reaction was pressurized to 300 psig and heated to 160° C. while stirring at 1094 rpm. At 90° C. hydrogen consumption began and the pressure was increased to 600 psig. Although the hydrogen uptake appeared to stop after about 30 minutes, the reaction mass was allowed to remain under these conditions for another 60 minutes before cooling to room temperature for venting and discharge. Samples were taken periodically during the reaction and the progress of the reaction in Table 1.

TABLE 1

| Time (Minutes) | Normalized Weight Percent | |
|---|---|---|
| | PAS (Weight Percent) | CHAS (Weight Percent) |
| 30 | 8.4 | 87.7 |
| 60 | 4.1 | 91.7 |
| 90 | 3.7 | 92.0 |

PAS is N-phenyl-3-aminopropyltrimethoxysilane.
CHAS is N-cyclohexylaminopropyltrimethoxysilane.

Example 3

In a 2 liter autoclave containing a stirrer, cooling coil, and sampling tube was added 976.1 grams of N-phenyl-3-aminopropyltrimethoxysilane and 10.9 grams of 5% rhodium on carbon. After purging the autoclave with nitrogen and then hydrogen, the reaction was pressurized to 300 psig and heated to 160° C. while stirring at 1140 rpm. At 98.6° C. hydrogen consumption began and the pressure was increased to 600 psig. Although the hydrogen uptake appeared to stop after about 30 minutes, the reaction mass was allowed to remain under these conditions for another 120 minutes before cooling to room temperature for venting and discharge. Samples were taken periodically during the reaction and the progress of the reaction is shown in Table 2.

TABLE 2

| Time (Minutes) | Normalized Weight Percent | |
|---|---|---|
| | PAS (Weight Percent) | CHAS (Weight Percent) |
| 60 | 6.88 | 85.3 |
| 90 | 5.2 | 91.1 |
| 150 | 4.2 | 91.6 |

Example 4

In a 2 liter autoclave containing a stirrer, cooling coil, and sampling tube was added 900 grams of N-phenyl-3-aminopropyltrimethoxysilane and 4 grams of 5% rhodium on carbon (G106N/D, lot: CC3-292, Degussa Corporation, Clavert City, Ky.). After purging the autoclave with nitrogen and then hydrogen, the reaction was pressurized to 400 psig and heated to 160° C. while stirring at 1103 rpm. At 87° C. hydrogen consumption began. Although the hydrogen uptake appeared to stop after about 30 minutes, the reaction mass was allowed to remain under these conditions for another 90 minutes before cooling to room temperature for venting and discharge. Samples were taken periodically during the reaction and the progress of the reaction is shown in Table 3.

TABLE 3

| Time (Minutes) | Normalized Weight Percent | |
|---|---|---|
| | PAS (Weight Percent) | CHAS (Weight Percent) |
| 30 | 2.0 | 93.9 |
| 60 | 0.2 | 96.1 |
| 120 | None Detected | 94.1 |

Example 5

In a 2 liter autoclave containing a stirrer, cooling coil, and sampling tube was added 972.3 grams of N-phenyl-3-aminopropyltrimethoxysilane and 1 gram of 5% rhodium on carbon (G106N/D, lot: CC3-292, Degussa Corporation, Clavert City, Ky.). After purging the autoclave with nitrogen and then hydrogen, the reaction was pressurized to 300 psig and heated to 160° C. while stirring at 1094 rpm. At 99° C., hydrogen consumption began. Although the hydrogen uptake appeared to stop after about 30 minutes, the reaction mass was allowed to remain under these conditions for another 90 minutes before cooling to room temperature for venting and discharge. Samples were taken periodically during the reaction and the progress of the reaction is shown in Table 4.

TABLE 4

| Time (Minutes) | Normalized Weight Percent | |
|---|---|---|
| | PAS (Weight Percent) | CHAS (Weight Percent) |
| 30 | 28.1 | 68.4 |
| 60 | 1.1 | 95.05 |
| 120 | None Detected | 96.2 |

Example 6

Catalyst Recycle

In a 2 liter autoclave containing a stirrer, cooling coil, and sampling tube was added 968.7 grams of N-phenyl-3-aminopropyltrimethoxysilane and 5.1 grams of 5% rhodium on S carbon recycled from examples 3 and 4 by filtration. After purging the autoclave with nitrogen and then hydrogen, the reaction was pressurized to 300 psig and heated to 160° C. while stirring at 1118 rpm. At 87° C. hydrogen consumption began. Although the hydrogen uptake appeared to stop after about 30 minutes, the reaction mass was allowed to remain under these conditions for another 30 minutes before cooling to room temperature for venting and discharge. Samples were taken periodically during the reaction and the progress of the reaction is shown in Table 5.

TABLE 5

| | Normalized Weight Percent | |
|---|---|---|
| Time (Minutes) | PAS (Weight Percent) | CHAS (Weight Percent) |
| 30 | 3.1 | 92.9 |
| 60 | 0.3 | 96.3 |

Example 7

Preparation of N,N'-(1,4-Phenylenedimethylidyne) bis-1-propanamine

In a 3 liter, two-necked glass round bottomed flask equipped with a magnetic stirrer, 324 grams (2.4 moles) of terephthaldicarboxaldehyde (Aldrich Chemical Co., Milwaukee, Wis.) was mixed with 1000 grams of toluene with stirring. To this mixture was added 311 grams (5.3 moles) of n-propyl amine(Aldrich Chemical Co., Milwaukee, Wis.) dropwise over a two hour period keeping the temperature below 50° C. The resulting cloudy solution was stirred at room temperature for 12 hours before the lower aqueous layer was removed. The organic layer was concentrated under vacuum to yield 479.6 grams (2.2 moles) of a clear, yellow oil, 92.5% isolated yield.

Example 8

Preparation of N,N'-(1,4-Phenylenedimethylidyne) bis[3-(trimethoxysilyl)-1-propanamine In a 2 liter single necked round bottom flask, 479.6 grams of N,N'-(1,4-phenylenedimethylidyne)bis-1-propanamine was combined with 918.9 grams (5.1 moles) of 3-aminopropyltrimethoxysilane (Silquest A-I 110 Silane, OSi Specialties, Sistersville, W.Va.). The resulting solution was concentrated under vacuum at 70° C. for three hours to yield 691.2 grams (1.5 moles) of N,N'-(1,4-phenylenedimethylidyne)bis{3-(trimethoxysilyl)-1-propanamine}, in 68.8% yield. Structure was verified by mass spectrometry and proton and carbon NMR.

Example 9

N,N'-(1,4-Dimethylcyclohexyl)bis[3-(trimethylsilyl) 1-propanamine

In a 2 liter autoclave containing a stirrer, cooling coil, and sampling tube was added 1081.8 grams of N,N'-(1,4-phenylenedimethylidyne)bis[3-(trimethoxysilyl)-1-propanamine and 1.0 gram of 5% rhodium on carbon [G106N/D, lot: CC3-292, Degussa Corporation, Clavert City, Ky.]. After purging the autoclave with nitrogen and then hydrogen, the reaction was pressurized to 300 psig and heated to 160° C. while stirring at 1076 rpm. At 96° C. hydrogen consumption began. Although the hydrogen uptake appeared to stop after about 30 minutes, the reaction mass was allowed to remain under these conditions for another 60 minutes before cooling to room temperature for venting and discharge. Samples were taken periodically during the reaction and the progress of the reaction is shown in Table 6.

TABLE 6

| | Normalized Weight Percent | | | |
|---|---|---|---|---|
| Time (Minutes) | PAS (wt. %) | SM (wt. %)) | Product (wt. %) | DMCH (wt. %) |
| 0 | 26.8 | 60.8 | None Detected | None Detected |
| 30 | 31.3 | 8.0 | 27.1 | .5 |
| 60 | 25.3 | 1.5 | 20.9 | 8.6 |
| 90 | 30 | None Detected | 22.3 | 12.5 |

PAS (primary amino silane) is 3-aminopropyltrimethoxysilane.
SM is N,N'-(1,4-phenylenedimethylidyne)bis{3-(trimethoxysilyl)-1-propanamine.
Product is N,N'-(1,4-dimethylcyclohexyl)bis{3-(trimethoxysilyl)-1-propanamine}.
DMCH is dimethylcyclohexane.

In view of the many changes and modifications that can be made without departing from principles underlying the invention, reference should be made to the appended claims for an understanding of the scope of the protection to be afforded the invention.

What is claimed is:

1. A process for the synthesis of N-cycloalkylaminoalkylsilanes comprising hydrogenating the corresponding N-arylaminoalkylsilanes in the presence of a catalytically effective amount of a supported or unsupported catalyst selected from the group consisting of palladium, platinum, nickel, rhenium, rhodium, ruthenium, copper chromite, and mixtures of the foregoing.

2. The process of claim 1 wherein the catalyst is supported.

3. The process of claim 2 wherein the support for the catalyst is selected from the group consisting of carbon, carbonates, kieselguhr, alumina, and silica.

4. The process of claim 3 wherein the support is carbon.

5. The process of claim 1 wherein the catalyst is selected from the group consisting of rhodium, ruthenium, and mixtures thereof.

6. The process of claim 2 wherein the catalyst is selected from the group consisting of rhodium, ruthenium, and mixtures thereof.

7. The process of claim 4 wherein the catalyst is rhodium.

8. The process of claim 1 wherein the aryl moiety of the N-arylaminoalkylsilane is selected from the group consisting of derivatives of benzene, toluene, xylene, indene, naphthalene, methylnaphthalene, diphenyl, acenaphthene, fluorene, phenanthrene,anthracene, fluoranthene, pyrene, chrysene, thiophene, pyridine, picoline, quinoline, isoquinoline, quinaldine, indole, furan, acridine, carbazole, diphenylene oxide, hemimellitene, mesitylene, prehnitene, isodurene, durene, pentamethylbenzene, ethylbenzene, propylbenzene, cumene, butylbenzene, cymene, triethylbenzene, styrene, allylbenzene, stilbene, diphenylmethane, triphenylmethane, tetraphenylmethane, terphenyl, and quaterphenyl.

9. The process of claim 8 wherein the aryl moiety of the N-arylaminoalkylsilane is a phenyl group.

10. The process of claim 1 wherein the N-arylaminoalkylsilane is selected from the group consisting of N-phenyl-γ-aminopropyltrimethoxysilane; N-phenyl-γ-aminopropyltributoxysilane; N-phenyl-γ-aminopropyltridodecyloxysilane; N-phenyl-γ-amino-2-methylpropyltrimethoxysilane; N-(4-trimethylsilyloxy)-phenyl-γ-aminopropyltrimethoxysilane; N-(4-N,N-dimethylaminophenyl)-γ-aminopropyltrimethoxysilane;

4,4'-oxybis{N-[3-(triethoxysilyl)propyl]-benzenamine}; m-{3-(trimethoxysilylpropyl)amino}aniline; p-{3-(trimethoxysilylpropyl)amino}aniline; p-{3-(triethoxysilylpropyl)amino}aniline; 3,5-dimethyl-N-{3-(trimethoxysilyl)propyl}-benzenamine; 4-methyl-N-{3-(triethoxysilyl)propyl}benzenamine; 4-methyl-N-{3-(trimethoxysilyl)propyl}benzenamine, 4-methyl-N-{3-(trimethoxysilyl)propyl}-1,3-benzenediamine, and N-{3-(triethoxysilyl)propyl}-1-naphthylamine.

* * * * *